United States Patent
Werbitzky

[11] Patent Number: 5,892,044
[45] Date of Patent: Apr. 6, 1999

[54] PROCESS FOR PREPARING OPTICALLY ACTIVE 1-(P-METHOXYBENZYL)-1,2,3,4,5,3,7,8-OCTAHYDROISOQUINOLINE

[75] Inventor: Oleg Werbitzky, Visp, Switzerland

[73] Assignee: Lonza Ltd., Gampel/Valais, Switzerland

[21] Appl. No.: 981,584

[22] PCT Filed: Jul. 3, 1996

[86] PCT No.: PCT/EP96/02923

§ 371 Date: Dec. 31, 1997

§ 102(e) Date: Dec. 31, 1997

[87] PCT Pub. No.: WO97/03052

PCT Pub. Date: Jan. 30, 1997

[30] Foreign Application Priority Data

Jul. 11, 1995 [CH] Switzerland .............. 2025/95
Mar. 5, 1996 [CH] Switzerland .............. 570/96

[51] Int. Cl.⁶ ................................. C07D 217/20
[52] U.S. Cl. ............................................ 546/139
[58] Field of Search ............................. 546/139

[56] References Cited

FOREIGN PATENT DOCUMENTS

| | | |
|---|---|---|
| 0 176 856 | 9/1986 | European Pat. Off. |
| 0 307 168 | 3/1989 | European Pat. Off. |
| 0564406 | 3/1993 | European Pat. Off. |
| 0 564 406 A1 | 6/1993 | European Pat. Off. |
| 0612758 | 2/1994 | European Pat. Off. |
| 0 612 758 A1 | 8/1994 | European Pat. Off. |
| 3436179 | 4/1986 | Germany . |
| 170924 | 4/1978 | Hungary . |
| 5-92958 | 4/1993 | Japan . |

OTHER PUBLICATIONS

O. Schnider et al., Helv. Chim. Acta, 37, (1954), 710.
A. Brossi and O. Schnider, Helv. Chim. Acta, 39, (1956), 1376.
T. Morimoto et al., Tetrahedron Lett., 30, (1989), 735.
T. Hayashi et al., Bull. Chem. Soc. Jpn., vol. 53, No. 4, (Apr. 1980), 1138 to 1151 (Hayashi et al. II).
T. Hayashi et al. J. Of Organometallic Chemistry, vol. 413, No. 1 to 3, (Aug. 7, '91), 295 to 302, (Hayashi et al. I).

*Primary Examiner*—Zinna Northington Davis
*Attorney, Agent, or Firm*—Fisher, Christen & Sabol

[57] ABSTRACT

Optically active 1-(p-methoxybenzyl)-1,2,3,4,5,6,7,8-octahydroisoquinoline having the formula (I) is prepared by asymmetric hydrogenation of the corresponding 3,4,5,6,7,8-hexahydro-compound or of the new 1-(p-methoxybenzyl)-3,4,5,6,7,8-hexahydroisoquinoline dihydrogenated phosphate in the present of chiral iridium-phosphine complexes. This product is an intermediate product in the synthesis of cough-relieving dextromethorphanne and analgesic levorphanol.

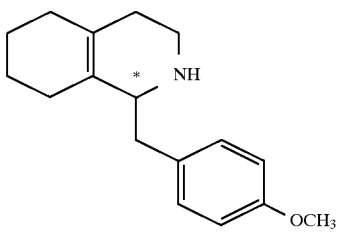

29 Claims, No Drawings

PROCESS FOR PREPARING OPTICALLY ACTIVE 1-(P-METHOXYBENZYL)-1,2,3,4,5,3, 7,8-OCTAHYDROISOQUINOLINE

This application is a 371 of PCT/EP96/02923, filed on Jul. 3, 1996.

BACKGROUND OF THE INVENTION

1. Field of the Invention

The present invention relates to a process for the preparation of 1-(p-methoxybenzyl)-1,2,3,4,5,6,7,8-octahydroisoquinoline of the formula

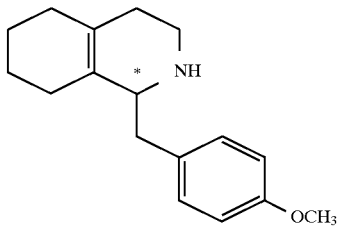

in optically active form by asymmetric hydrogenation.

It further relates to a novel salt of 1-(p-methoxybenzyl)-3,4,5,6,7,8-hexahydroisoquinoline and a process for its preparation.

It also relates to a novel chiral diphosphine having a ferrocene structure and to its use for the preparation of catalysts for asymmetric hydrogenation, to the iridium-phosphine complexes obtainable from the diphosphine and also to a novel chiral amino-phosphine having a ferrocene structure as intermediate in the synthesis of the diphosphine.

2. Background Art 1-(p-Methoxybenzyl)-1,2,3,4,5,6,7,8-octahydroisoquinoline (I) is an intermediate in the synthesis of the antitussive dextromethorphan and the analgesic levorphanol. The targeted preparation of the effective enantiomer of dextromethorphan requires I in the (S)-(−)-configuration, and the synthesis of levorphanol requires I in the (R)-(+)-configuration. A classical process for obtaining these stereoisomers is racemate resolution, which, in this case, is also possible without the use of optically active ancillary reagents (DE-A 34 36 179). The main disadvantage of almost all racemate resolutions is that at least half of the substance used has to be disposed of as waste in the form of the "undesired" enantiomer unless, exceptionally, it too is required in comparable quantities. In the present case, racemization is also possible, meaning that the undesired enantiomer can be recycled as racemate and there are in theory no losses (O. Schnider et al., Helv. Chim. Acta 1954, 37, 710; A. Brossi, O. Schnider, Helv. Chim. Acta 1956, 39, 1376; HU 170 924). This method is, however, rather involved.

A significantly better strategy is the targeted synthesis through a stereoselective reaction, starting from a prochiral precursor. It is known that N-acyl-1-benzylidene-1,2,3,4,5,6,7,8-octahydroisoquinolines can be stereoselectively ("asymmetrically") hydrogenated at the exocyclic double bond using chiral ruthenium-phosphine complexes (JP-A 05/092 958). This process does, however, have the disadvantage that an N-acylated product is obtained whose acyl group has to be cleaved off again in a further synthesis step. Furthermore, the benzylidene compounds are for their part formed as E/Z-isomer mixtures, of which in each case only the Z-isomer can be used for the stereoselective hydrogenation.

BROAD DESCRIPTION OF THE INVENTION

The object of the present invention was, therefore, to provide a straightforward process which produces the title compound directly in good optical purity.

According to the invention, the object is achieved by the process of the invention.

It has been found that by using optically active iridium-phosphine complexes as catalysts, 1-(p-methoxybenzyl)-3,4,5,6,7,8-hexahydroisoquinoline of the formula

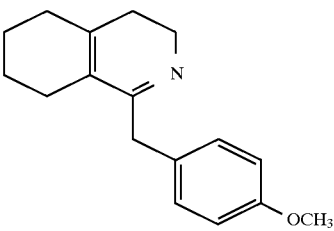

or a salt thereof can be directly hydrogenated asymmetrically to give the S- or R-enantiomers of the title compound. The nature and configuration of the catalyst determine which enantiomer is formed in preference and how high the optical yield is. The optically active iridium-phosphine complexes which may be used are, in principle, any chiral complexes of iridium in low oxidation state which have polydentate chiral phosphines as ligands, are able to coordinate with hydrogen and are catalytically active. For the hydrogenation, it is possible to use both neutral and cationic iridium-phosphine complexes as catalysts. These catalysts can also be produced in situ. In this case, the active catalyst is formed directly in the hydrogenation reaction by ligand-exchange from a precursor complex of iridium, the corresponding chiral ligand and hydrogen. The precursor complex used can, for example, be a complex of the general formula $[Ir_2(L_c)_2Cl_2]$, where $L_c$ is a $C_{4-12}$-diene. In this case, a neutral complex is obtained. If, on the other hand, a complex of the general formula $[Ir(L_c)_2]^+BF_4^-$, where $L_c$ is as defined above, is used, for example, a cationic complex is formed.

Preference is given to using pre-formed cationic complexes of the general formula $$[IrL_cL_p]^+A^- \qquad III$$

which, with hydrogen, form the actual catalytically active species. In this connection, $L_c$ is a $C_{4-12}$-diene, $L_p$ is a chiral bidentate phosphine and $A^-$ is an anion. Here, bidentate phosphines are taken to mean not only diphosphines, but also phosphines which contain a second non-phosphorus coordinating atom, such as, for example, amino-phosphines. The $A^-$ anion is preferably a non-coordinating or only a weakly coordinating anion, such as, for example, tetrafluoroborate, hexafluorophosphate, hexafluoroantimonate, perchlorate, phosphate, acetate, trifluoroacetate, trifluoromethanesulfonate or toluene-4-sulfonate.

The $L_c$ diene which may be present can, for example, be norbornadiene or, preferably, 1,5-cyclooctadiene.

Examples of bidentate chiral phosphine ligands $L_p$ are:
2,4-bis(diphenylphosphino)pentane (BDPP), 2-[phenyl-(3-sulfophenyl) phosphino]-4-(diphenylphosphino)pentane (BDPP-S),
2,3-bis(diphenylphosphino)butane (chiraphos), 4,5-bis(diphenylphosphino-methyl)-2,2-dimethyl-1,3-dioxolane (DIOP),
2,2'-bis(diphenylphosphino)-1,1'-binaphthalene (BINAP), 1-tert-butoxycarbonyl-4-diphenylphosphino-2-(diphenylphosphinomethyl)pyrrolidine (BPPM),
2,3-bis(diphenylphosphino)bicyclo[2.2.1]hept-5-ene (norphos),
1,2-bis-(2,5-dimethylphospholano)benzene (Me-DUPHOS), 1-benzyl-3,4-bis(diphenylphosphino) pyrrolidine (deguphos)

or bis(dimethylphosphino)cyclohexane (BDPPMC).

Depending on which of the two enantiomers of the bidentate chiral phosphine ligand is used, the R— or S— form of I can be prepared in a targeted manner.

The cationic complexes (III) can be prepared, for example, by reacting a complex of the general formula [Ir$_2$(L$_c$)$_2$Cl$_2$], where L$_c$ is a C$_{4-12}$-diene, with the desired bidentate chiral phosphine ligand and subsequently with a soluble silver salt which contains the desired A$^-$ anion. The chloride bonded coordinately in [Ir$_2$(L$_c$)$_2$Cl$_2$] is precipitated out as insoluble silver chloride.

The phosphine ligand L$_p$ used is preferably a ferrocenylphosphine of the general formula

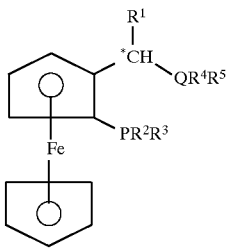

IV

Q is nitrogen or phosphorus, and R$^1$ is a C$_1$–C$_4$-alkyl group. R$^2$ to R$^5$ are in each case independently of one another C$_1$–C$_6$-alkyl, C$_3$–C$_7$-cycloalkyl or phenyl, which may have one or more substituents such as, for example, methyl, trifluoromethyl or methoxy.

Particular preference is given to phosphine ligands IV in which R$^1$ is methyl.

Particular preference is also given to phosphine ligands IV in which Q is phosphorus.

Particular preference is likewise given to phosphine ligands IV in which R$^2$ and R$^3$ are identical and are in each case a phenyl group or a substituted phenyl group.

Particular preference is further given to phosphine ligands IV in which R$^4$ and R$^5$ are identical and are C$_1$–C$_4$-alkyl, cyclohexyl or optionally substituted phenyl.

Examples of ferrocenylphosphines of the formula IV include:

(R)-1-[(S)-2-(diphenylphosphino) ferrocenyl]ethyl-di-tert-butylphosphine (Q=P, R$^1$=CH$_3$, R$^2$=R$^3$=C$_6$H$_5$, R$^4$=R$^5$=t-Bu) [(R, S)-PPF-PtBu$_2$], (R)-1-[(S)-2-(diphenylphosphino)ferrocenyl]ethyl-dicyclohexylphosphine (Q=P, R$^1$=CH$_3$, R$^2$=R$^3$=C$_6$H$_5$, R$^4$=R$^5$=cyclohexyl) [(R,S)-PPF-PCy$_2$], (R)-1-[(S)-2-(diphenylphosphino)ferrocenyl]ethyl-diphenylphosphine (Q=P, R$^1$=CH$_3$, R$^2$=R$^3$=R$^4$=R$^5$=C$_6$H$_5$) [(R,S)-PPF-PPh$_2$, (R)-1-{ (S)-2-[bis (4-methoxyphenyl)phosphino] ferrocenyl}ethyl-di-tert-butylphosphine (Q=P, R$^1$=CH$_3$, R$^2$=R$^3$=p-CH$_3$OC$_6$H$_4$, R$^4$ =R$^5$=t-Bu) [(R,S)-MeOPPF-PtBu$_2$], (R)-1-{(S)-2-[bis(4-trifluoromethylphenyl)phosphino]-ferrocenyl}ethyl-di-tert-butylphosphine (Q=P, R$^1$=CH$_3$, R$^2$=R$^3$=p-CF$_3$C$_6$H$_4$, R$^4$=R$^5$=t-Bu) [(R,S)-CF$_3$PPF-PtBu$_2$], (R)-1-[(S)-2-(di-p-tolylphosphino)ferrocenyl]ethyl-di-tert-butylphosphine (Q=P, R$^1$=CH$_3$, R$^2$=R$^3$=p-CH$_3$C$_6$H$_4$, R$^4$=R$^5$=t-Bu) ((R,S)-MePPF-PtBu$_2$], (R)-1-[(S)-2-(diphenylphosphino) ferrocenyl] ethyl-bis (4-methoxy-3,5-dimethylphenyl)phosphine (Q=P, R$^1$=CH$_3$, R$^2$=R$^3$=C$_6$H$_5$, R$^4$=R$^5$=4-methoxy-3,5-dimethylphenyl) [(R,S) -PPF-PMOD$_2$], N,N-dimethyl-{ (R)-1-[(S)-2-(diphenylphosphino) ferrocenyl]ethylamine} (Q=N, R$^1$=R$^4$=R$^5$=CH$_3$, R$^2$=R$^3$= C$_6$H$_5$) [(R,S)-PPFA], and their antipodes.

Some of these ferrocenylphosphines are known from EP-A 0 564 406, EP-A 0 612 758 and T. Hayashi et al., Bull. Chem. Soc. Jpn. 1980, 53, 1138–1151, and some can be obtained in a similar manner to the compounds described there.

Particularly good results were achieved with (R)-1-{(S)-2-[bis(4-methoxy-3,5-dimethylphenyl)-phosphino] ferrocenyl}ethyl-di-tert-butylphosphine (Q=P, R$^1$=CH$_3$, R$^2$=R$^3$=4-methoxy-3,5-dimethylphenyl, R$^4$=R$^5$=t-Bu) [(R, S)-MODPF-PtBu$_2$] as phosphine ligand IV. This diphosphine and its antipode are novel and are also provided by the present invention. They can be prepared by reacting the corresponding enantiomer of the known N-N-dimethyl-1-ferrocenylethylamine with n-butyllithium and bis(4-methoxy-3,5-dimethylphenyl)chlorophosphine to give the corresponding N,N-dimethyl-1-{2-[bis(4-methoxy-3,5-dimethylphenyl)phosphino]ferrocenyl}ethylamines and subsequently replacing the dimethylamino group with di-tert-butylphosphine.

The N,N-dimethyl-1-{2-[bis(4-methoxy-3,5-dimethylphenyl)phosphino]ferrocenyl}ethylamines are likewise novel compounds and provided by the present invention.

Of the iridium-phosphine complexes which can be obtained from (R)-1-{(S)-2-[bis(4-methoxy-3,5-dimethylphenyl)phosphino]ferrocenyl}ethyl-di-tert-butylphosphine and its antipode, preference is given to those which can be obtained by reaction with a complex of the general formula [Ir$_2$(L$_c$)$_2$Cl$_2$], where L$_c$ is a C$_{4-12}$-diene, preferably 1,5-cyclooctadiene or norbornadiene, and subsequently with a silver salt from the group consisting of silver tetrafluoroborate, hexafluorophosphate, hexafluoroantimonate, perchlorate, acetate, trifluoroacetate, trifluoromethanesulfonate or toluene-4-sulfonate.

Particular preference is given to those iridium-phosphine complexes in which L$_c$ is 1,5-cyclooctadiene and the silver salt is silver tetrafluoroborate.

The asymmetric hydrogenation is advantageously carried out at a temperature of from −20° C. to 100° C., preferably from 10° C. to 40° C., and at a pressure of from 1 bar to 200 bar, preferably from 10 to 100 bar.

Examples of suitable solvents are aromatic hydrocarbons, such as benzene or toluene, ethers, such as diethyl ether, tetrahydrofuran or dioxane, chlorinated hydrocarbons, such as dichloromethane or dichloroethane, alcohols, such as methanol, ethanol or isopropyl alcohol, esters, such as ethyl acetate or butyl acetate and mixtures of these solvents with one another or with water. Preference is given to using toluene as a mixture with methanol or water (2 phases).

The stereoselectivity of the hydrogenation can be increased through additives. Examples thereof include inorganic or organic acids, such as phosphoric acid, hydrochloric acid, hydrobromic acid, hydroiodic acid, acetic acid or trifluoroacetic acid, amines, such as triethylamine, phosphines, such as triphenyl phosphine, or quarternary ammonium or phosphonium compounds, such as tetraethyl- or tetra-n-butylammonium fluoride, chloride, bromide, iodide or hydroxide, the corresponding quaternary ammonium salts of succinimide, or the analogous phosphonium salts.

The starting material 1-(p-methoxybenzyl)-3,4,5,6,7,8-hexahydroisoquinoline is very unstable and readily disproportionates. It is therefore preferably used in the form of a salt. Particular preference is given to the acidic salt of phosphoric acid, namely 1-(p-methoxybenzyl)-3,4,5,6,7,8-hexahydroisoquinolinium dihydrogenphosphate of the formula

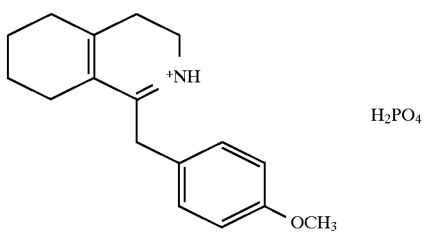

This novel compound is likewise provided by the invention. It is obtainable in crystalline form, is stable on storage and easy to prepare. Because of the amphoteric character of the dihydrogen phosphate ion, the compound also acts as a buffer and thus ensures that an optimum pH is maintained during hydrogenation.

The salt is advantageously prepared by cyclizing the N-[2-(cyclohexen-1-yl)ethyl]-p-methoxyphenylacetamide disclosed in U.S. Pat. No. 4,496,762 by heating with phosphorus oxychloride in a Bischler-Napieralski reaction, and then reacting with orthophosphoric acid in an organic solvent. Examples of suitable organic solvents in this connection are ethanol, acetone, toluene or mixtures of these solvents, optionally with the addition of a little water. Crystallization of the salt can be significantly improved by seeding. It is also important to carry out salt formation as soon as possible after cyclization in order to avoid decomposition of the free base.

DETAILED DESCRIPTION OF THE INVENTION

The following examples illustrate how the invention is carried out but are not intended to impose any limitation. In each case only the reaction with one of the two enantiomers of the catalyst is described.

Using the other enantiomer under the same reaction conditions can of course give the product having the opposite configuration.

EXAMPLES

Example 1

1-(p-methoxybenzyl)-3,4,5,6,7,8-hexahydroisoquinoline 27.3 g (0.1 mol) of N-[2-(cyclohexen-1-yl)ethyl]-p-methoxyphenylacetamide and 91.4 g (0.596 mol) of phosphorus oxychloride in 230 ml of toluene were heated to 100° C. under argon for 30 min. The mixture was then evaporated in a rotary evaporator, and the residue (46 g) was washed twice with 70 ml of petroleum ether and then dissolved in 270 ml of dichloromethane. The solution was added to 270 ml of a 12% strength aqueous ammonia solution at 0° C. with vigorous stirring. The organic phase was washed with 90 ml of water, dried over sodium sulfate and evaporated, giving 27.0 g of a viscous yellow-brown oil, which was used immediately for the hydrogenation.

$^1$H NMR (CDCl$_3$) δ=7.1 (d, 2H, aryl-H); 6.8 (d, 2H, aryl-H); 3.8 (s, 3H, OCH$_3$); 3.6 (s, 2H, CH$_2$Ar); 3.5 (t, 2H, CH$_2$N); 2.1–2.0 (m, 4H); 1.9 (m, 2H); 1.6–1.5 (m, 4H).

Example 2

1-(p-methoxybenzyl)-3,4,5,6,7,8-hexahydroisoquinolinium dihydrogen phosphate 27.0 g of crude 1-(p-methoxybenzyl)-3,4,5,6,7,8-hexahydroisoquinoline (prepared as in Example 1) were dissolved in 100 ml of ethanol. The solution was seeded with crystals of 1-(p-methoxybenzyl)-3,4,5,6,7,8-hexahydroisoquinolinium dihydrogenphosphate and admixed with a solution of 12.68 g of 85 strength orthophosphoric acid in 20 ml of ethanol with stirring and cooling. The solution was cooled to 0° C. and filtered. The precipitate was washed with ethanol and dried.

Yield: 23.19 g (65.6%); m.p.: 128.9° C.; $^1$H NMR (CDCl$_3$) δ=7.25 (d, 2H, aryl-H); 7.02 (d, 2H, aryl-H); 4.02 (s, 2H, CH$_2$Ar); 3.85 (s, 3H, OCH$_3$); 3.65 (t, 2H, CH$_2$N); 2.55 (t, 2H); 2.4 (m, 2H); 2.3 (m, 2H) 1.7–1.6 (m, 4H); $^{13}$C NMR (D$_2$O, int. Standard Dioxane) δ=179.0 (s); 161.1 (s); 159.7 (s); 131.8 (d); 125.7 (s); 124.6 (s); 115.4 (d); 56.3 (q); 40.4 (t); 31.9 (t); 27.6 (t); 24.2 (t); 22.2 (t); 21.4 (t).

Example 3

Preparation of the catalyst (III, L$_c$=η$^4$-1,5-cyclo-octadiene, L$_p$=IV, Q=P, R$^1$=CH$_3$, R$^2$=R$^3$=C$_6$H$_5$, R$^4$=R$^5$=t-Bu, A$^-$=BF$_4^-$)

1 g (1.49 mmol) of di-μ-chloro-bis(η$^4$-1,5-cyclo-octadiene)diiridium(I) was dissolved in 27 ml of dichloromethane under argon. 1.65 g (3.13 mmol) of (R)-1-[(S)-2-(diphenylphosphino)ferrocenyl]ethyl-di-tert-butylphosphine were added to this solution. The pale red solution was admixed with 0.592 g (2.98 mmol) of silver tetrafluoroborate in 9 ml of acetone. The reaction mixture was stirred for 1 hour at room temperature, the precipitated silver chloride was filtered off and the filtrate was evaporated under reduced pressure. The red-brown residue was washed and dried under reduced pressure.

Yield: 2.74 g (99%); $^1$H NMR (CDCl$_3$) δ=8.25 (dd, 2H); 7.75 (m, 3H); 7.5–7.4 (m, 5H); 5.5 (br. m, 1H); 5.4 (br. m, 1H); 4.7 (m, 1H); 4.5 (m, 1H); 4.3 (m, 1H); 3.9 (br. m, 1H); 3.7 (s, 5H); 3.4 (br. m, 1H); 3.15 (br. m, 1H); 2.2 (dd, 3H); 2.2–2.0 (br. m, 2H); 1.7 (d, 9H); 1.3 (d, 9H); 1.9–1.2 (br. m, 6H); $^{31}$P NMR (CDCl$_3$, 160 MHz) δ=61.95 (d, PtBu$_2$); −9.97 (d, PPh$_2$).

Example 4

(S)-(−)-1-(p-methoxybenzyl)-1,2,3,4,5,6,7,8-octahydroisoquinoline

An autoclave was charged with 35.4 g (0.1 mol) of 1-(p-methoxybenzyl)-3,4,5,6,7,8-hexahydroisoquinolinium dihydrogen phosphate (prepared as in Example 2) and 62.0 mg (66.6 μmol, corresponding to a starting material/catalyst ratio=1500) of catalyst (from Example 3) and also 38.2 mg (133.4 μmol) of tetrabutylammonium chloride After the air had been carefully removed from the closed autoclave and replaced by argon, 120 ml of oxygen-free toluene and a likewise oxygen-free solution of 4.4 g (0.11 mol) of sodium hydroxide in 40 ml of water were added. Hydrogen was injected until a pressure of 70 bar was reached, and the mixture was stirred at room temperature for 20 h. The aqueous phase was adjusted to pH>9 by adding sodium hydroxide and, following phase separation, was extracted using a further 100 ml of toluene. The combined organic phases were dried over sodium sulfate and evaporated under reduced pressure. The product was obtained as a yellow-brown viscous oil.

Yield: 23.5 g (91.7%); [α]$_D^{25}$=−118 (c=1, MeOH);
The optical purity was determined by HPLC on Chiracel® OD (Daicel).

ee=80% $^1$H NMR (CDCl$_3$) δ=7.15 (d, 2H, aryl-H); 6.8 (d, 2H, aryl-H); 3.8 (s, 3H, OCH$_3$); 3.25 (br. d, 1H); 3.1–2.9 (m, 2H); 2.75 (m, 1H); 2.45 (dd, 1H); 2.2–2.1 (m, 1H); 2.0–1.5 (m, 9H).

Example 5

(S)-(−)-1-(p-methoxybenzyl)-1,2,3,4,5,6,7,8-octahydroisoquinoline (catalyst preparation in situ)

Solutions of 1.28 g (5 mmol) of 1-(p-methoxybenzyl)-3,4,5,6,7,8-hexahydroisoquinoline in 10 ml of oxygen-free toluene and of 8.4 mg (12.5 μmol) of di-μ-chloro-bis-(η$^4$-1,5-cyclooctadiene)diiridium(I) and 14.9 mg (27.5 μmol) of (R)-1-[(S)-2-(diphenylphosphino)-ferrocenyl]ethyl-di-tert-butylphosphine in 9 ml of oxygen-free toluene and 1 ml of oxygen-free methanol were prepared. Both solutions were introduced via cannulae into a 50 ml-autoclave from which air had been carefully removed. Hydrogen was then injected until a pressure of 70 bar was reached. The reaction mixture was stirred at room temperature for 21 h and then evaporated under reduced pressure.

Yield: 1.21 g $[\alpha]_D^{25}$=−102 (c=1, MeOH); ee=82.5% (HPLC);

Example 6

N,N-Dimethyl-(R)-1-{(S)-2-[bis(4-methoxy-3,5-dimethylphenyl)phosphino]ferrocenyl}ethylamine Bis(4-methoxy-3,5-dimethylphenyl)chlorophosphine was prepared by reacting bis(3,5-dimethyl-4-methoxyphenyl)phosphinous acid (T. Morimoto et al., Tetrahedron Lett. 1989, 30, 735) with phosphorus trichloride and distilling the reaction product at 185° C./0.2 mbar. 1.71 g (5.82 mmol) of (R)-N,N-dimethyl-1-ferrocenylethylamine were dissolved in 11 ml of tert-butyl methyl ether under argon. 3.5 ml (8.75 mmol) of n-butyllithium (2.5M solution in hexane) were added dropwise, and then a solution of 2.94 g (8.73 mmol) of bis(4-methoxy-3,5-dimethylphenyl) chlorophosphine in 5 ml of tert-butyl methyl ether was added. The brown reaction mixture was heated to 50° C. and stirred for a further 4 h. After the mixture had cooled to 0° C., 0.35 g of NaHCO$_3$ in 7 ml of water was slowly added. 10 ml of dichloromethane were added and then the reaction mixture was filtered and the insoluble residue was washed with a further 10 ml of dichloromethane. The aqueous phase was extracted three times with 5 ml of dichloromethane and the combined organic phases were washed with 5 ml of water, dried over sodium sulfate and evaporated. The brown oily crude product (4.3 g) was recrystallized from 14 ml of ethanol.

Yield: 0.98 g (30.2%) of a brown solid $[\alpha]_D^{25}$=−272.4 (c=0.4; CHCl$_3$); $^1$H NMR (CDCl$_3$, 400 MHz) δ=1.28 (d, 3H, CH(NMe$_2$)CH$_3$); 1.8 (s, 6H, NMe$_2$), 2.18 (s, 6H, PhCH$_3$); 2.32 (s, 6H, PhCH$_3$); 3.62 (s, 3H, OCH$_3$); 3.72 (s, 3H, OCH$_3$); 3.85 (S, 1H, C$_5$H$_3$); 3.92 (s, 5H, C$_5$H$_5$); 4.06 (q, 1H, CHNMe$_2$); 4.22 (s, 1H, C$_5$H$_3$); 4.35 (s, 1H, C$_5$H$_3$); 6.82 (d, 2H$_1$, C$_6$H$_2$); 7.25 (d, 2H, C$_6$H$_2$); $^{31}$P NMR (CDCl$_3$, 160 MHz) δ=−23.7

Example 7

(R)-1-{(S)-2-[bis (4-methoxy-3,5-dimethylphenyl)phosphino]ferrocenyl}ethyl-di-tert-butylphosphine 0.979 g (1.76 mmol) of N,N-dimethyl-(R)-1-{(S)-2-[bis(4-methoxy-3,5-dimethylphenyl)phosphino]ferrocenyl}ethylamine (prepared as in Example 6) was suspended in 18 ml of acetic acid under argon. 0.345 g (2.36 mmol) of di-tert-butylphosphine was then added and the reaction mixture was stirred at 80° C. for 2.5 h. The reaction solution was evaporated under reduced pressure, giving 1.3 g of a red-brown oil which was chromatographed over a silica gel column using ethyl acetate/hexane/ethanol (47.5: 47.5:5).

Yield: 0.9 g (77%) of an orange-red solid $[\alpha]_D^{25}$=−324.6 (c=0.4; CHCl$_3$); $^1$H NMR (CDCl$_3$, 400 MHz) δ=0.97 (d, 9H; tBu) 1.15 (d, 9H; tBu); 1.82 (dd, 3H, CHPtBu$_2$CH$_3$); 2.18 (s, 6H, PhCH$_3$); 2.25 (s, 6H, PhCH$_3$); 3.35 (q, 1H, CHPtBu$_2$); 3.62 (s, 3H, OCH$_3$); 3.72 (s, 3H, OCH$_3$); 3.88 (s, 5H, C$_5$H$_5$); 3.95 (s, 1H, C$_5$H$_3$); 4.2 (s, 1H, C$_5$H$_3$); 4.35 (s, 1H, C$_5$H$_3$); 6.82 (d, 2H, C$_6$H$_2$); 7.3 (d, 2H, C$_6$H$_2$); $^{31}$P NMR (CDCl$_3$, 160 MHz) δ=49.3 (d, $^4J_{pp}$=44.5 Hz, PtBu$_2$); −26.7 (d, $^4J_{pp}$=44.5 Hz, PPh$_2$).

Example 8

Preparation of the catalyst:

115 mg (170.8 μmol) of di-μ-chloro-bis(η$^4$-1,5-cyclooctadiene)diiridium(I) were dissolved in 3.4 ml of dichloromethane under argon. 250 mg (379.6 μmol) of (R)-1-{(S)-2-[bis(3,5-dimethyl-4-methoxyphenyl)-phosphino]-ferrocenyl}ethyl-di-tert-butylphosphine (prepared as in Example 7) were added to this solution at 0° C. The pale red solution was admixed with 67.9 mg (341.6 μmol) of silver tetrafluoroborate in 1.1 ml of acetone. The reaction mixture was stirred at 0° C. for 1 h, the precipitated silver chloride was filtered off and the filtrate was evaporated under reduced pressure. The red-brown residue was washed with diethyl ether and dried under reduced pressure.

Yield: 350 mg (98%) $^1$H NMR (CDCl$_3$, 400 MHz) δ=7.95 (d, 2H); 7.05 (d, 2H); 5.6 (br. s, 1H); 5.25 (br. s, 1H); 4.7 (s, 1H); 4.5 (s, 1H); 4.3 (s, 1H); 3.84 (s, 3H); 3.82 (s, 3H); 3.78 (s, 5H); 3.7 (br. s, 1H); 3.3 (br. s, 2H); 2.45 (s, 6H); 2.3 (s, 6H); 2.2 (dd, 3H); 2.3–2.1 (br. m, 2H); 1.65 (d, 9H); 1.25 (d, 9H); 2.0–1.5 (br. m, 6H); $^{31}$P NMR (CDCl$_3$, 160 MHz) δ=61.5 (d, PtBu); −7.45 (d, PPh$_2$)

Example 9

(S)-1-(p-methoxybenzyl)-1,2,3,4,5,6,7,8-octahydroisoquinoline

An autoclave was charged with 3.54 g (10 mmol) of 1-(p-methoxybenzyl)-3,4,5,6,7,8-hexahydroisoquinolinium dihydrogenphosphate (prepared as in Example 2) and 6.97 mg (6.66 μmol, corresponding to a starting material/catalyst ratio=1500) of catalyst from Example 8 and also 8.68 mg of tetrabutylammonium bromide. After the air had been carefully removed from the closed autoclave and replaced by argon, 14 ml of oxygen-free toluene and a likewise oxygen-free solution of 440 mg of sodium hydroxide in 40 ml of water were added. Hydrogen was injected until a pressure of 70 bar was reached, and the mixture was stirred at room temperature for 22 h. The aqueous phase was adjusted to pH>9 by adding sodium hydroxide and, following phase separation, was extracted with a further 10 ml of toluene. The combined organic phases were dried over sodium sulfate and evaporated under reduced pressure. The product was obtained as a yellow-brown oil.

Yield: 2.32 g (90.2%) $[\alpha]_D^{25}$=−131.7 (c=1, MeOH); The optical purity was determined by HPLC on Chiracel® OD (Daicel). ee=89.2%.

Examples 10–24

The reactions summarized in Table 1 below were carried out as described under Examples 4 and 5. The "Starting material" column gives the formula numbers of the starting materials used. The "P" column gives the precursor complex used. "A" represents Ir(cod)L$_p$ (prepared as in Example 3) (cod=1,5-cyclooctadiene) and "B" represents [Ir$_2$(cod)$_2$Cl$_2$]. The abbreviations listed in the "Ligand" column correspond to the abbreviations given in brackets in the above list of ligands. The "SM/C" column gives the molar ratio of starting material: catalyst. "RT" is room temperature. The abbreviations used in the "Additives" column are in detail:
TBACL=tetra-n-butylammonium chloride
TBAF=tetra-n-butylammonium fluoride
TBAI=tetra-n-butylammonium iodide
TBASI=tetra-n-butylammonium, salt with succinimide
TBPBr=tetra-n-butylphosphonium bromide
TEAH=tetraethylammonium hydroxide

TABLE 1

| Starting material | P | Ligand | SM/C | Solvent | Temp. | p [bar] | Additives | ee [%] |
|---|---|---|---|---|---|---|---|---|
| 30 mmol V | A | (R,S)-PPF-PtBu$_2$ | 600 | 80 ml dioxane/6.3 ml H$_2$O | RT | 70 | 2.0 mmol TBACl, 24 mmol NaOH, 24 mmol TEAH | 85.4 (S) |
| 30 mmol V | A | (R,S)-PPF-PtBu$_2$ | 1000 | 38 ml toluene/10 ml H$_2$O | RT | 10 | 0.12 mmol TBACl, 33 mmol NaOH | 79.1 (S) |
| 20 mmol II | A | (R,S)-PPF-PtBu$_2$ | 800 | 19 ml toluene/1 ml MeOH | RT | 70 | 6.66 mmol H$_3$PO$_4$ | 71.1 (S) |
| 5 mmol II | B | (R,S)-PPF-PtBu$_2$ | 200 | 19 ml toluene/1 ml MeOH | RT | 70 | | 85.2 (S) |
| 10 mmol V | A | (R,S)-PPF-PtBu$_2$ | 3000 | 14 ml toluene/3.3 ml H$_2$O | RT | 70 | 11 mmol NaOH, 13.3 mmol TBAI | 35.8 (S) |
| 10 mmol V | A | (R,S)-MODPF-PtBu$_2$ | 1500 | 7 ml toluene/7 ml dioxane/3.3 ml H$_2$O | RT | 70 | 11 mmol NaOH, 13.3 mmol TBAI | 75.8 (S) |
| 5 mmol II | B | (+)-Norphos | 100 | 10 ml toluene/10 ml MeOH | RT | 70 | | 30.7 (S) |
| 5 mmol II | B | (R,R)-Chiraphos | 100 | 2 ml toluene/18 ml MeOH | RT | 70 | | 38.4 (R) |
| 5 mmol II | B | (R,S)-PPF-Pcy$_2$ | 100 | 20 ml MeOH | RT | 70 | | 53.9 (R) |
| 5 mmol II | B | (R,R)-BDPP-S | 100 | 20 ml MeOH | 0° C. | 70 | | 16.7 (S) |
| 5 mmol II | B | (+) – (S,S) BDPPMC | 100 | 20 ml MeOH | RT | 70 | | 18.9 (S) |
| 5 mmol II | B | (+) – (S,S) BDPPMC | 100 | 20 ml toluene | RT | 70 | | 16.7 (R) |
| 10 mmol V | A | (R,S)-PPF-PtBu$_2$ | 1000 | 14 ml toluene, 3.3 ml H$_2$O | RT | 70 | 11 mmol NaOH, 40 μmol TBPBr | 79.7 (S) |
| 10 mmol V | A | (R,S)-PPF-PtBu$_2$ | 1000 | 14 ml toluene, 3.3 ml H$_2$O | RT | 70 | 11 mmol NaOH, 40 μmol TBAF | 82.5 (S) |
| 10 mmol V | A | (R,S)-PPF-PtBu$_2$ | 1000 | 14 ml toluene, 3.3 ml H$_2$O | RT | 70 | 11 mmol NaOH, 40 μmol TBASI | 79.6 (S) |

I claim:

1. Process for the preparation of optically active 1-(p-methoxybenzyl)-1,2,3,4,5,6,7,8-octahydroisoquinoline of the formula

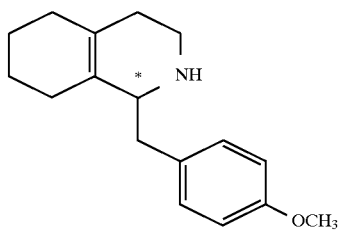

I wherein 1-(p-methoxybenzyl)-3,4,5,6,7,8-hexahydroisoquinoline of the formula

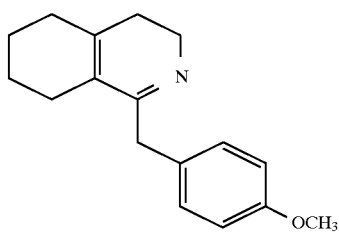

II or a salt thereof is asymmetrically hydrogenated in the presence of a catalytically effective optically active iridium-phosphine complex.

2. Process according to claim 1, wherein the catalytically effective optically active iridium-phosphine complex is formed from a complex of the formula

$[IrL_cL_p]^+A^-$    III or from the reaction product of $[Ir(L_c)_2Cl_2]$ or $[Ir(L_c)_2]^+$ $BF_4^-$ and $L_p$, where in each case $L_c$ is $C_{4-12}$-diene, $L_p$ is a chiral bidentate phosphine and $A^-$ is an anion.

3. Process according to claim 2, wherein $L_p$ is 1,5-cyclooctadiene.

4. Process according to claim 2, wherein $L_p$ is a ferrocenylphosphine of the formula

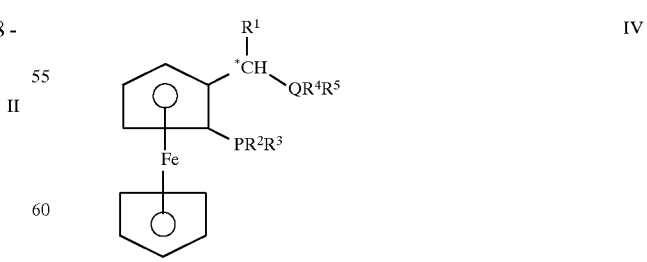

IV where Q is nitrogen or phosphorus, $R^1$ is a $C_{1-4}$-alkyl group, and $R^2$ to $R^5$ are independently of one another $C_{1-6}$-alkyl, $C_{3-7}$-cycloalkyl or optionally substituted phenyl.

5. Process according to claim 4, wherein $R^1$ is methyl.

6. Process according to claim 5, wherein Q is phosphorus.

7. Process according to claim 6, wherein $R^2$ and $R^3$ are identical and are phenyl or substituted phenyl.

8. Process according to claim 7, wherein $R^2$ and $R^3$ are 4-methoxy-3,5-dimethylphenyl.

9. Process according to claim 8, wherein $R^4$ and $R^5$ are identical and are $C_{1-4}$-alkyl, cyclohexyl or optionally substituted phenyl.

10. Process according to claim 9, wherein the $L_p$ ligand is (R)-1-{(S)-2-[bis(4-methoxy-3,5-dimethylphenyl) phosphino]ferrocenyl}ethyl-di-tert-butyl-phosphine or its antipode.

11. Process according to claim 10, wherein that 1-(p-methoxybenzyl)-3,4,5,6,7,8-hexahydroisoquinoline is used in the form of the dihydrogenphosphate of the formula:

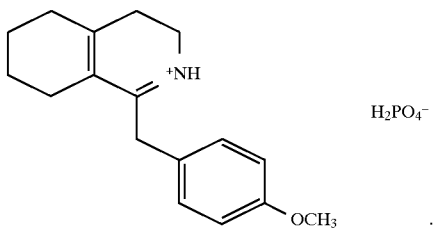

V

12. Process according to claim 10, wherein 1-(p-methoxybenzyl)-3,4,5,6,7,8-hexahydroisoquinoline is used in the form of the dihydrogenphosphate of the formula:

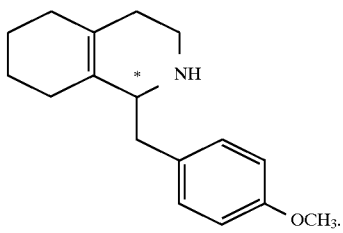

I

13. Process for the preparation of 1-(p-methoxybenzyl)-3,4,5,6,7,8-hexahydroisoquinolinium dihydrogenphosphate, wherein N-[2-(cyclohexen-1-yl)ethyl]-p-methoxyphenylacetamide is cyclized by heating with phosphorus oxychloride and then reacted with orthophosphoric acid in an organic solvent.

14. (R)-1-{(S)-2-[bis(4-methoxy-3,5-dimethylphenyl)-phosphino]ferrocenyl)ethyl-di-tert-butylphosphine.

15. (S)-1-{(R)-2-[bis(4-methoxy-3,5-dimethylphenyl)-phosphino]ferrocenyl}ethyl-di-tert-butylphosphine.

16. Process according to claim 4, wherein Q is phosphorus.

17. Process according to claim 4, wherein $R^2$ and $R^3$ are identical and are phenyl or substituted phenyl.

18. Process according to claim 4, wherein $R^4$ and $R^5$ are identical and are $C_{1-4}$-alkyl, cyclohexyl or optionally substituted phenyl.

19. Process according to claim 4, wherein the $L_p$ ligand is (R)-1-{(S)-2-[bis(4-methoxy-3,5-dimethylphenyl) phosphino]ferrocenyl}ethyl-di-tert-butyl-phosphine or its antipode.

20. Process according to claim 1, wherein 1-(p-methoxybenzyl)-3,4,5,6,7,8-hexahydroisoquinoline is used in the form of the dihydrogenphosphate of the formula:

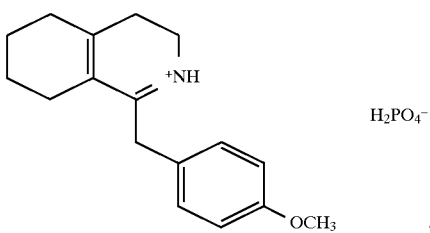

V

21. Process according to claim 1 for the preparation of an iridium-phosphine complex comprising reacting a complex of the formula $[Ir_2(L_c)_2Cl_2]$, where $L_c$ is a $C_{4-12}$-diene with the (R)-1-{(S)-2-[bis(4-methoxy-3,5-dimethylphenyl) phosphino]ferrocenyl}ethyl-di-tert-butylphosphine and a silver salt from the group consisting of silver tetraflurorborate, hexafluorophosphate, hexaflucroantimonate, perchlorate, acetate, trifluoroacetate, trifluoromethanesulfonate or toluene-4-sulfonate.

22. Process according to claim 21 wherein $L_c$ is 1,5-cyclooctadiene or norbornadiene.

23. Process according to claim 1 wherein the iridium-phosphine complex which has been prepared by reacting a complex of the formula $[Ir_2(L_c)_2Cl_2]$, where $L_c$ is a $C_{4-12}$-diene with the (R)-1-{(S)-2-[bis(4-methoxy-3,5-dimethylphenyl)phosphino]ferrocenyl}ethyl-di-tert-butylphosphine and a silver salt from the group consisting of silver tetraflurorborate, hexafluorophosphate, hexafluoroantimonate, perchlorate, acetate, trifluoroacetate, trifluoromethanesulfonate or toluene-4-sulfonate.

24. Process according to claim 1 for the preparation of an iridium-phosphine complex comprising reacting a complex of the formula $[Ir_2(L_c)_2Cl_2]$, where $L_c$ is a $C_{4-12}$-diene with the (S)-1-{(R)-2-[bis(4-methoxy-3,5-dimethylphenyl) phosphino]ferrocenyl}ethyl-di-tert-butylphosphine and a silver salt from the group consisting of silver tetraflurorborate, hexafluorophosphate, hexafluoroantimonate, perchlorate, acetate, trifluoroacetate, trifluoromethanesulfonate or toluene-4-sulfonate.

25. Process according to claim 24 wherein $L_c$ is 1,5-cyclooctadiene or norbornadiene.

26. Process according to claim 1 wherein the iridium-phosphine complex which has been prepared by reacting a complex of the formula $[Ir_2(L_c)_2Cl_2]$, where $L_c$ is a $C_{4-14}$-diene with the (S)-1-{(R)-2-[bis(4-methoxy-3,5-dimethylphenyl)phosphino]ferrocenyl}ethyl-di-tert-butylphosphine and a silver salt from the group consisting of silver tetraflurorborate, hexafluorophosphate, hexafluoroantimonate, perchlorate, acetate, trifluoroacetate, trifluoromethanesulfonate or toluene-4-sulfonate.

27. Iridium-phosphine complex according to claim 23, wherein $L_c$ is 1,5-cyclooctadiene and the silver salt is silver tetrafluoroborate.

28. Process according to claim 26, wherein $L_c$ is 1,5-cyclooctadiene or norbornadiene.

29. N-N-Dimethyl-(S)-1-{(R)-2-[bis(4-methoxy-3,5-dimethylphenyl)phosphino]ferrocenyl}-ethylamine.

* * * * *